(12) United States Patent
Timoszyk et al.

(10) Patent No.: US 12,364,637 B2
(45) Date of Patent: Jul. 22, 2025

(54) MEDICAL WASTE MANAGEMENT SYSTEM INTEGRATED WITHIN A MEDICAL FACILITY

(71) Applicant: Stryker Corporation, Kalamazoo, MI (US)

(72) Inventors: Wojciech Kazimierz Timoszyk, Flower Mound, TX (US); Brian MacLachlan, Norton Shores, MI (US); Stephen J. Reasoner, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 480 days.

(21) Appl. No.: 17/298,864

(22) PCT Filed: Nov. 27, 2019

(86) PCT No.: PCT/US2019/063563
§ 371 (c)(1),
(2) Date: Jun. 1, 2021

(87) PCT Pub. No.: WO2020/117587
PCT Pub. Date: Jun. 11, 2020

(65) Prior Publication Data
US 2022/0031927 A1 Feb. 3, 2022

Related U.S. Application Data

(60) Provisional application No. 62/775,579, filed on Dec. 5, 2018.

(51) Int. Cl.
*A61G 13/10* (2006.01)
*A61M 1/00* (2006.01)

(52) U.S. Cl.
CPC ............. *A61G 13/102* (2013.01); *A61M 1/60* (2021.05); *A61M 1/63* (2021.05); *A61M 1/74* (2021.05);
(Continued)

(58) Field of Classification Search
CPC ......... A61G 13/102; A61M 1/60; A61M 1/63; A61M 1/74; A61M 2205/3389;
(Continued)

(56) References Cited

U.S. PATENT DOCUMENTS

| 3,782,384 A | 1/1974 | Timmermans |
| 6,770,061 B2 | 8/2004 | Wildman |

(Continued)

FOREIGN PATENT DOCUMENTS

| CN | 101370535 A | 2/2009 |
| CN | 101597320 A | 12/2009 |

(Continued)

OTHER PUBLICATIONS

International Search Report for Application No. PCT/US2019/063563 dated Jul. 7, 2020, 4 pages.

(Continued)

*Primary Examiner* — Ariana Zimbouski
*Assistant Examiner* — Eric Rassavong
(74) *Attorney, Agent, or Firm* — Howard & Howard Attorneys PLLC

(57) ABSTRACT

A medical waste management system including a boom secured to a fixed structure of a medical facility. A waste container defines a waste volume sized to collect liquid waste material received through a suction line under the influence of a vacuum provided by a vacuum pump. The system may include a service head coupled to the boom and including the waste container. A vacuum port is in fluid communication with the waste volume, and discharge and/or cleaning ports also in communication with the waste volume may be provided. The vacuum pump may be integrated with the medical facility, and the system may include an offload pump Integrated with the medical facility and in communication with the discharge port. The waste container may be (Continued)

supported on a mobile cart configured to be removably coupled with the boom. The system may further include a liquid measuring system coupled to the waste container.

11 Claims, 9 Drawing Sheets

(52) U.S. Cl.
CPC .............. *A61M 2205/3389* (2013.01); *A61M 2205/587* (2013.01); *A61M 2209/082* (2013.01); *A61M 2209/10* (2013.01)

(58) Field of Classification Search
CPC ...... A61M 2205/587; A61M 2209/082; A61M 2209/10; A61M 2205/27; A61M 2205/60; A61B 2090/5025; A61B 90/50
See application file for complete search history.

(56) References Cited

U.S. PATENT DOCUMENTS

| | | | |
|---|---|---|---|
| 7,516,924 B2 | 4/2009 | White et al. | |
| 7,597,731 B2 | 10/2009 | Palmerton et al. | |
| 7,615,037 B2 | 11/2009 | Murray et al. | |
| 7,621,898 B2 | 11/2009 | Lalomia et al. | |
| 8,088,079 B2 | 1/2012 | Kaye et al. | |
| 8,506,798 B2 | 8/2013 | Beulay et al. | |
| 9,532,843 B2 | 1/2017 | Palmerton et al. | |
| 9,592,329 B2 * | 3/2017 | Pohlmeier | A61M 1/1656 |
| 9,782,524 B2 | 10/2017 | Reasoner et al. | |
| 10,034,673 B2 | 7/2018 | Lynch et al. | |
| 10,105,470 B2 | 10/2018 | Reasoner et al. | |
| 10,252,856 B2 | 4/2019 | Michaels et al. | |
| 10,343,102 B2 | 7/2019 | Reasoner et al. | |
| 2002/0111592 A1 | 8/2002 | Bemis et al. | |
| 2003/0164600 A1 * | 9/2003 | Dunn | B08B 9/093 |
| | | | 280/47.34 |
| 2005/0187529 A1 | 8/2005 | Reasoner et al. | |
| 2007/0135779 A1 * | 6/2007 | Lalomia | A61M 1/60 |
| | | | 604/319 |
| 2009/0012485 A1 | 1/2009 | Michaels et al. | |
| 2009/0101219 A1 | 4/2009 | Martini et al. | |
| 2010/0016817 A1 | 1/2010 | Cadoche Jacobson | |
| 2010/0206785 A1 | 8/2010 | Beulay et al. | |
| 2012/0016337 A1 * | 1/2012 | Khalaj | A61M 1/60 |
| | | | 604/506 |
| 2015/0224237 A1 * | 8/2015 | Reasoner | A61M 1/79 |
| | | | 604/320 |
| 2016/0367732 A1 | 12/2016 | Reasoner et al. | |
| 2017/0028110 A1 * | 2/2017 | Smith | A61M 1/73 |
| 2017/0281836 A1 | 10/2017 | Giezendanner et al. | |
| 2018/0221804 A1 | 8/2018 | Reasoner et al. | |
| 2018/0250088 A1 | 9/2018 | Brennan et al. | |
| 2018/0259122 A1 | 9/2018 | Reavill et al. | |
| 2018/0361033 A1 | 12/2018 | Reasoner et al. | |

FOREIGN PATENT DOCUMENTS

| | | |
|---|---|---|
| CN | 102475922 A | 5/2012 |
| CN | 202437772 U | 9/2012 |
| EP | 1480594 B1 | 8/2009 |
| GB | 2465951 B | 10/2012 |
| JP | 2007209764 A | 8/2007 |
| JP | 2009519757 A | 5/2009 |
| JP | 2010522061 A | 7/2010 |
| JP | 2019055224 A | 4/2019 |
| WO | 9900154 A1 | 1/1999 |
| WO | 2004075740 A1 | 9/2004 |
| WO | 2007103842 A2 | 9/2007 |
| WO | 2008118398 A1 | 10/2008 |
| WO | 2011113572 A1 | 9/2011 |
| WO | 2014066337 A2 | 5/2014 |
| WO | 2014117043 A1 | 7/2014 |
| WO | 2015164384 A1 | 10/2015 |
| WO | 2017112684 A1 | 6/2017 |

OTHER PUBLICATIONS

International Search Report for Application No. PCT/US2013/066101, dated May 23, 2014, 2 pages.
Partial International Search Report for Application No. PCT/US2019/063563 dated Mar. 18, 2020, 2 pages.
English language abstract for CN 101370535 extracted from espacenet.com database on Nov. 30, 2017, 2 pages.
English language abstract for CN 101597320 extracted from espacenet.com database on Nov. 30, 2017, 2 pages.
English language abstract and machine-assisted English translation for CN 102475922 extracted from espacenet.com database on Nov. 30, 2017, 7 pages.
English language abstract and machine-assisted English translation for CN 202437772 extracted from espacenet.com database on Nov. 30, 2017, 5 pages.
English language abstract for JP 2007-209764 extracted from espacenet.com database on Nov. 30, 2017, 1 page.
English language abstract for JP 2009-519757 A extracted from espacenet.com database on Jun. 10, 2021, 2 pages.
English language abstract for JP 2012-522061 A extracted from espacenet.com database on Jun. 10, 2021, 2 pages.
English language abstract for JP 2019-055224 A extracted from espacenet.com database on Jun. 10, 2021, 2 pages.
English language abstract for WO 2004/075740 extracted from espacenet.com database on Nov. 30, 2017, 2 bages.
English language abstract for WO 2011/113572 extracted from espacenet.com database on Mar. 28, 2018, 2 pages.
Youtube, "Serres Nemo Video", https://www.youtube.com/watch?v=RGIXcIKdIQU., Oct. 27, 2015, 3 pages.

* cited by examiner

MEDICAL WASTE MANAGEMENT SYSTEM INTEGRATED WITHIN A MEDICAL FACILITY

REFERENCE TO RELATED APPLICATION

This application is the National Stage entry of International Patent Application No. PCT/US2019/063563, filed Nov. 27, 2019, which claims priority to and all the benefits of U.S. Provisional Patent Application No. 62/775,579, filed Dec. 5, 2018, the entire contents of which are hereby incorporated by reference.

BACKGROUND

During surgical procedures performed within a medical facility, a byproduct may include waste material, for example, blood or other bodily fluids, resected tissue, smoke, and the like. In certain instances, a waste collection assembly may be provided to collect the waste material within a waste container under the influence of suction. One known implementation is disclosed in commonly owned U.S. Pat. No. 7,621,898, issued Nov. 24, 2009, hereby incorporated by reference in its entirety. The waste container is disposed on a wheeled cart to be movably positioned near the operating table within the operating suite. The portability of the wheeled cart provides convenience and flexibility in positioning the waste collection assembly as desired; however, the footprint of the waste collection assembly occupies valuable floor space within the operating room. Therefore, there is a need in the art for a medical waste management system configured to be integrated with a medical facility in a manner to preserve space. Further, it would be desirable to integrate certain subsystems of the waste collection assembly with the medical facility to potentially provide for a simpler construction and/or operation of the waste collection assembly.

SUMMARY

A medical waste management system configured to be integrated with a medical facility. The system includes a mount configured to be rigidly secured to a fixed structure of the medical facility, and a boom secured to the mount. The boom includes at least one elongated arm for extending away from the fixed structure. A service head is coupled to the boom, and a waste container is located on the service head. The waste container defines a waste volume sized to collect liquid waste material during a medical procedure performed within the medical facility. The liquid waste material is received through a suction line under the influence of a vacuum provided by a vacuum pump. A vacuum port is in fluid communication with the waste volume. The vacuum port is configured to be coupled to a vacuum line to establish fluid communication between the waste volume and the vacuum pump. A liquid measuring system coupled to the waste container within the waste volume. The liquid measuring system is configured to measure a level of the liquid waste material within the waste volume. The liquid measuring system is optional.

A medical waste management system configured to be integrated with a medical facility. The system includes a mount configured to be rigidly secured to a fixed structure of the medical facility, and a boom secured to the mount. The boom includes at least one elongated arm for extending away from the fixed structure. The system includes a mobile cart having a base and wheels coupled to the base for moving the mobile cart along a floor surface of the medical facility. A waste container is supported on the mobile cart. The waste container defines a waste volume sized to collect liquid waste material during a medical procedure performed within the medical facility. The liquid waste material is received through a suction line under the influence of a vacuum provided by a vacuum pump. A vacuum port is in fluid communication with the waste volume. The vacuum port is configured to be coupled to a vacuum line to establish fluid communication between the waste volume and the vacuum pump. Each of the mobile cart and the boom includes a complementary coupling mechanism configured to removably couple the mobile cart with the boom to establish the fluid communication between the waste volume and the vacuum pump.

A medical waste management system configured to be integrated with a medical facility. The system includes a vacuum pump and an offload pump. A mount is configured to be secured to a fixed structure of the medical facility, and a boom is secured to the mount. The boom includes at least one elongated arm for extending away from the fixed structure. A service head is secured to the at least one elongated arm and includes a waste container. The waste container defines a waste volume sized to collect liquid waste material during a medical procedure performed within the medical facility. A vacuum line is in fluid communication with the waste volume and the vacuum pump. The vacuum pump is operable to draw a vacuum through the vacuum line such that the liquid waste material is drawn through a suction line coupled to the waste container and into the waste volume. A discharge line is in fluid communication with the waste volume and the offload pump. The offload pump is operable to draw another vacuum through the discharge line such that the liquid waste material collected in the waste volume is directed to a disposal system integrated with the medical facility.

A method for operating a medical waste management system is also disclosed. The system includes a vacuum pump and an offload pump integrated with a medical facility. A mount is configured to be secured to a fixed structure of the medical facility, and a boom secured to the mount. The boom includes at least one elongated arm. A service head is secured to the at least one elongated arm and includes a waste container defining a waste volume. A vacuum line is in fluid communication with the waste volume and the vacuum pump. A discharge line is in fluid communication with the waste volume and the offload pump. The vacuum pump is operated to draw a vacuum through the vacuum line such that liquid waste material is drawn through a suction line coupled to the waste container and into the waste volume. The offload pump is operated to draw another vacuum such that the liquid waste material is drawn from the waste container and through the discharge line within the at least one elongated arm of the boom to a discharge system integrated with the medical facility.

A method for operating a medical waste management system is also disclosed. The system includes a vacuum pump and an offload pump integrated with a medical facility. A mount is configured to be secured to a fixed structure of the medical facility, and a boom secured to the mount. The boom includes at least one elongated arm. A service head is secured to the at least one elongated arm and includes a waste container defining a waste volume, and a coupling mechanism. A vacuum line is in fluid communication with the waste volume and the vacuum pump. A disposal system is integrated with the medical facility and includes an offload pump. A discharge line in fluid communication with the offload pump. An inlet port is disposed on the fixed structure or another fixed structure of the medical facility and in fluid communication with the discharge line. The vacuum pump is operated to draw a vacuum through the vacuum line such that the liquid waste material is drawn through a suction line coupled to the waste container and into the waste volume. The operation of the vacuum pump is stopped. The boom is moved such that the waste container with the waste material within the waste volume is in proximity with the inlet port. The coupling mechanism of the service head is removably engaged with a complementary coupling mechanism of the discharge system to establish fluid communication between the waste volume, the inlet port, and the discharge line. The offload pump is operated to draw another vacuum such that the liquid waste material is drawn from the waste container and through the discharge line.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
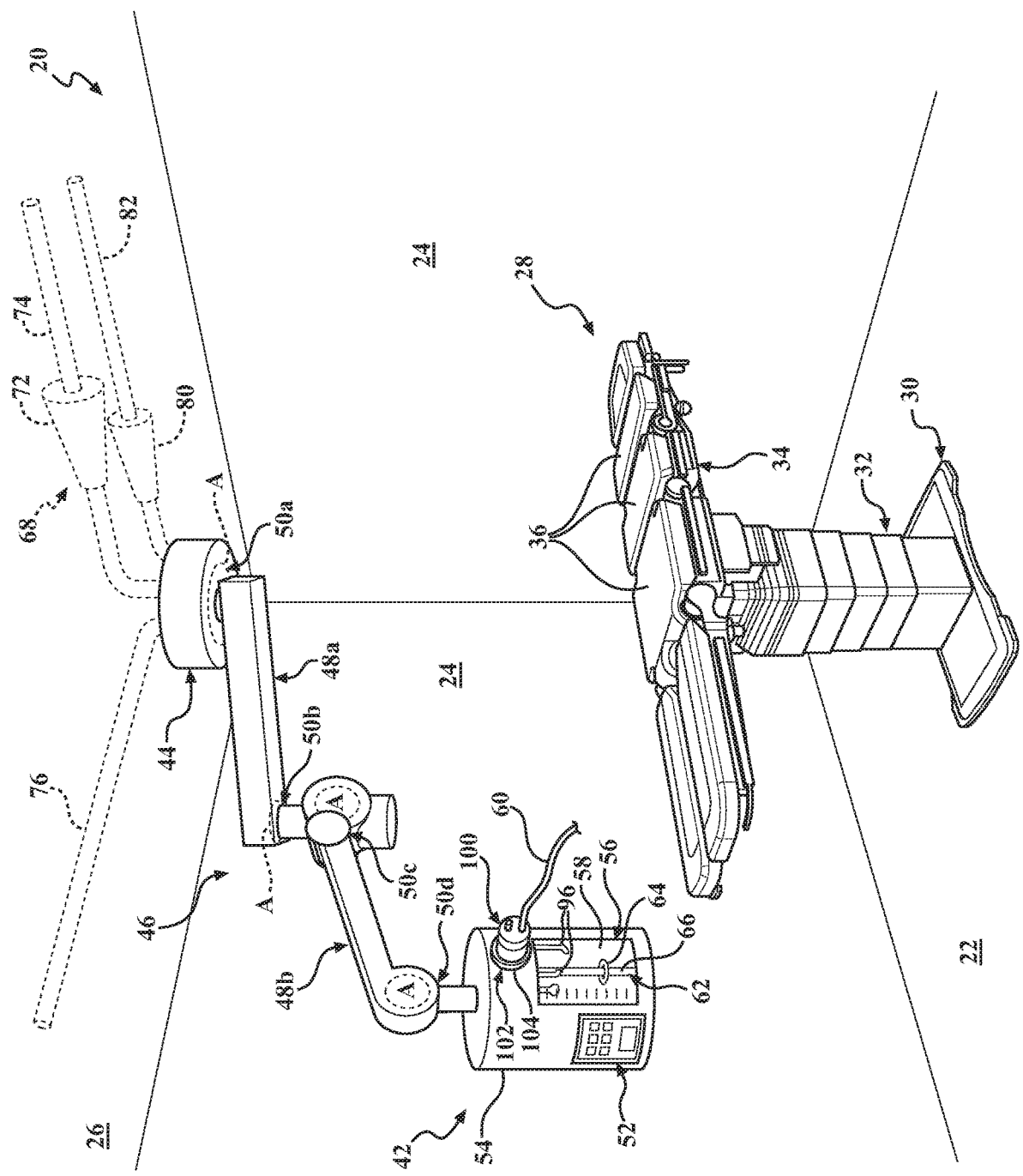
FIG. 1 is a perspective view of a medical facility and a medical waste management system.

FIG. 1 is a perspective view of a medical facility 20, and more particularly an operating room, including a floor surface 22, walls 24, and a ceiling 26 collectively defining the room. A patient support apparatus 28 is supported on the floor surface 22. The patient support apparatus 28 may include a base 30, an intermediate frame 32, a patient support deck 34, and one or more sections collectively defining a patient support surface 36 for supporting a patient (not shown). The base 30 may be rigidly coupled to the floor surface 22, as shown, or may be movable along with the floor surface 22 with wheels or the like. The intermediate frame 32 generally extends upwardly from the base 30. FIG. 1 shows the intermediate frame 32 being represented by telescoping sections with internal mechanisms (not shown) providing for adjustment of the elevation of the patient support surface 36 relative to the floor surface 22. The sections of the patient support deck 34 and the patient support surface 36 may be configured to move and/or articulate relative to one another to facilitate proper patient positioning on the patient support surface 36. The present disclosure contemplates any suitable construction of the patient support apparatus 28.

With continued reference to FIG. 1, an implementation of a medical waste management system 40 is shown within the medical facility 20. The medical waste management system 40 may include a waste collection assembly 42 integrated with the medical facility 20 in a manner that, among other advantages to be described, preserves valuable floor space and provides for ease of operation. The medical waste management system 40 includes a mount 44 configured to be rigidly secured to a fixed structure of the medical facility 20. The fixed structure may be the floor surface 22 (see FIG. 7), the wall(s) 24, and/or the ceiling 26 (see FIGS. 1, 3, 6, 8 and 9). FIG. 1 shows the mount 44 rigidly secured to the ceiling 26. The mount 44 may be rigidly secured to the fixed structure through any suitably sturdy joining means such that the weight of the waste collection assembly 42 is supported by the fixed structure and/or other architecture of the medical facility 20.

The medical waste management system 40 may include a boom 46 secured to the mount 44. The boom 46 includes at least one elongated arm 48a, 48b extending away from the fixed structure. The elongate arms 48a, 48b are formed from materials with sufficient mechanical characteristics to support the weight of the waste collection assembly 42. The illustrated boom 46 includes two elongated arms 48a, 48b coupled to one another with one or more joints 50b, 50c to provide relative articulation between the elongated arms 48a, 48b. Likewise, a first of the elongated arms 48a is coupled to the mount 44 at a first joint 50a providing for articulation of the first elongated arm 48a relative to the mount 44, and the waste collection assembly 42 is coupled to a second of the elongated arms 48b at a fourth joint 50d providing for articulation of the waste collection assembly 42 relative to the second elongated arm 48b. More specifically, a first end of the first elongated arm 48a may be coupled to the mount 44 at a revolute joint; a second end of the first elongated arm 48a coupled to the a first end of the second elongated arm 48b at two revolute joints arranged orthogonal to one another; and a second end of the second elongated arm coupled to the waste collection assembly 42 at another revolute joint. It is appreciated that the boom 46 may include any number and/or type of arms, joints, and the like, providing for any two-dimensional or three-dimensional movement of the waste collection assembly 42 relative to the fixed structure of the medial facility 20. Suitable joints may include a prismatic joint, cylindrical joint, spherical joint, planar joint, among others. Suitable arms may be linear, arcuate, segmented, or the like. For example, a prismatic joint may provide for a telescopic arrangement between segments of one or more of the elongated arms 48a, 48b. The above-described boom 46 including two elongated arms 48a, 48b and four joints 50a-50d is merely exemplary. In another implementation, the boom 46 may be a multi-link structure including at least three horizontally aligned members relatively rotatable about each other, for example, the arrangement disclosed in commonly owned United States Patent Publication No. 2018/0259122, published Sep. 13, 2018, the entire contents of which are hereby incorporated by reference.

The joints 50a-50d may provide for manual positioning of the waste collection assembly 42 within the medical facility 20. In other words, the joints 50a-50d are designed with suitable characteristics (e.g., friction, backdrive) to permit a user to, for example, provide a manual input to move the waste collection assembly 42 to a desired position, and maintain the desired position once the manual input is removed. Additionally or alternatively, one or more of the joints 50a-50d may be associated with an actuator A in communication with a controller (not shown) to provide motorized lift to and manipulation of the service head 54. In another implementation, springs (e.g., pneumatic springs) provide counterbalancing to the weight of the service head 54 to facilitate manual manipulation of the boom 46 without a motor. The user may provide an input to a user interface 52, for example, the user interface on a service head 54 of the waste collection assembly 42, after which the controller controls one or more of the actuators A to facilitate relative articulation between the elongated arms 48*a*, 48*b* to the desired position. The user interface, or a supplemental user interface, may also be arranged on the wall 24 of the medical facility 20 (see FIGS. 6 and 8), a mobile cart 116 (see FIG. 3), a support frame 144 (see FIG. 7), and/or on a personal device such as a tablet, smartphone, or the like. The user interface 52 is configured to receive an input from the user and display information to the user.

The waste collection assembly 42 will now be described with reference to FIGS. 1 and 2. The waste collection assembly 42 includes the service head 54 generally defining an overall form factor. FIG. 1 shows the service head 54 as substantially cylindrical, but other suitable form factors are contemplated. The service head 54 is coupled to the boom 46, for example, the second end of the second elongate arm 48*b*. The waste collection assembly 42 includes a waste container 56 disposed on or within the service head 54 and defining a waste volume 58 sized to collect liquid waste during a medical procedure performed within the medical facility 20. In particular, the waste volume 58 receives the liquid waste material through a suction line 60 under the influence of a vacuum provided by a vacuum pump 80 to be described. FIG. 1 shows at least a portion of the suction line 60 coupled to the waste collection assembly 42 to be in fluid communication with the waste volume 58. At a distal end of the suction line 60, an instrument 61 (see FIG. 4) including a suction tip may be positioned near the surgical site to collect the liquid waste material, for example, blood or other bodily fluids, under the influence of the vacuum. It is appreciated that smoke may also be collected along with the liquid waste material, but the waste volume 58 is sized to accommodate at least more than minimal amounts of liquid waste associated with the surgical procedure. In one example, the waste volume 58 of the waste container 56 is sized to accommodate three or more liters of the liquid waste material.

The waste container 56 is at least partially disposed within/on the service head 54. As shown in FIG. 1, a portion of the waste container 56 is formed from at least partially transparent material to optionally define a window viewable by the user. The user may quickly ascertain a volume of the liquid waste collected within the waste volume 58, and/or remaining capacity of the waste container 56. Should the user not wish to see the contents of the waste volume 58, a slidable door (not shown) or other suitable means (e.g., electrochromic glass) may be provided to selectively remove the waste volume 58 from view.

A waste collection assembly 42 of the medical waste management system 40 may include a liquid measuring system 62 configured to measure a level of the liquid waste material within the waste volume 58. The liquid measuring system 62 may be coupled to the waste container 56 within the waste volume 58. A liquid measuring system suitable for the present application disclosed in commonly owned United States Patent Publication No. 2018/0221804, filed Jan. 18, 2018, hereby incorporated by reference in its entirety, includes a float element 64 slidable along a sensor rod 66. The liquid measuring system 62 is in communication with the controller with the controller configured to receive signals from the liquid measuring system 62 indicative of the level of the liquid waste material. The controller may transmit a corresponding signal to the user interface 52 to display the level. The liquid measuring system 62 is not required and may be considered an optional component of the waste collection assembly 42.

Figure 2:
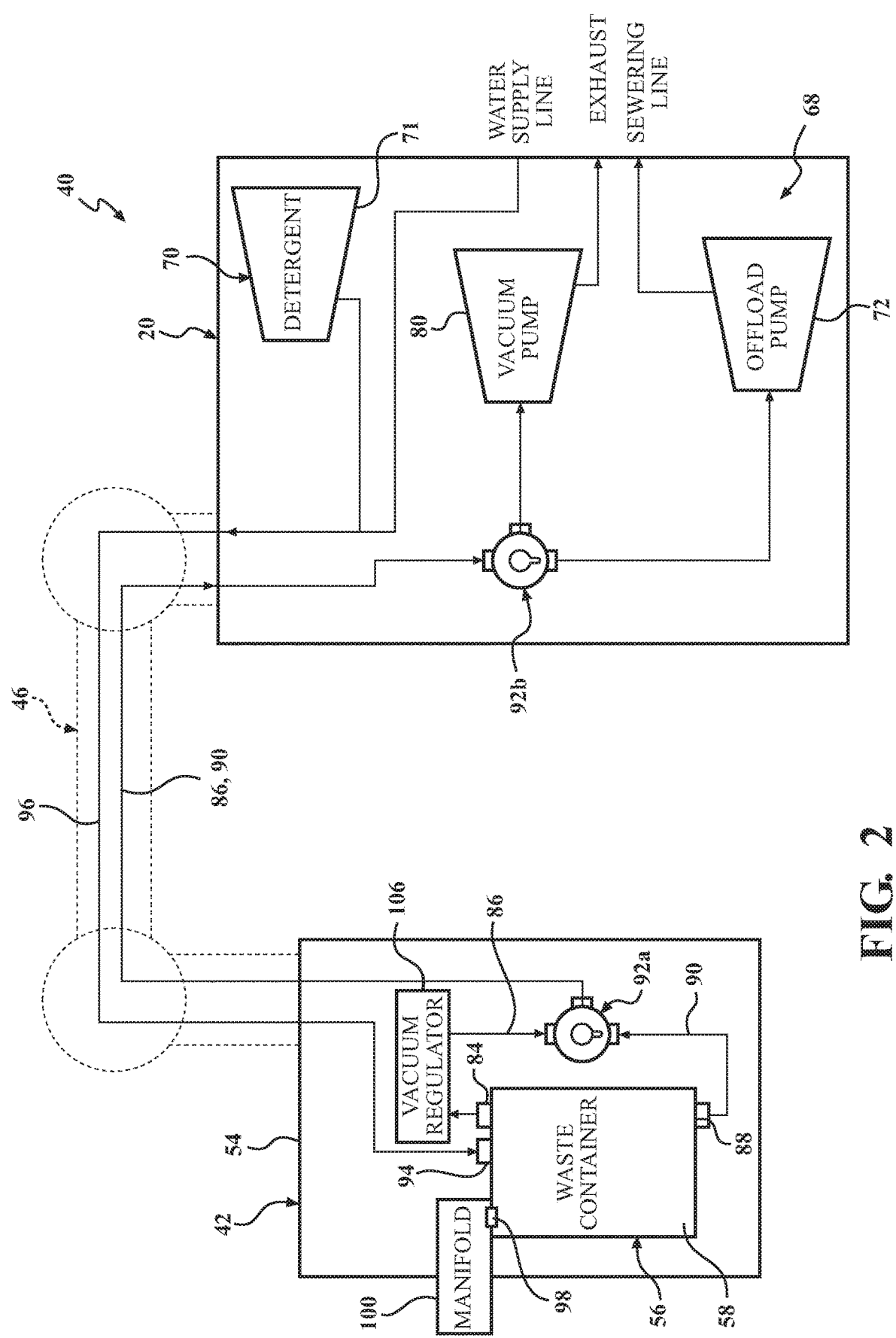
FIG. 2 is a schematic representation of the medical waste management system of FIG. 1.

With continued reference to FIGS. 1 and 2, the medical waste management system 40 includes a disposal system 68, a cleaning system 70, and the vacuum pump 80 at least partially fixed within the medical facility 20 facilitate integration of the medical waste management system 40. The disposal system 68 includes an offload pump 72 in communication with a sewering line 74. In manners to be further described, the offload pump 72 is configured to draw a vacuum on the waste volume 58 to direct the liquid waste material collected in the waste volume 58 to the sewering line 74. The sewering line 74 may be integrated with a municipal sewerage system, and/or with a second waste container (not shown) situated away from the medical facility 20. The cleaning system 70 includes a water supply line 76 that may be integrated with plumbing of the medical facility 20, for example, the municipal water system, and/or with a water reservoir situated away from the medical facility 20. The cleaning system 70 may also include a detergent reservoir 71 in fluid communication with the water supply line 76. The vacuum pump 80 may be in communication with an exhaust line 82 integrated with a ventilation system of the medical facility 20. FIG. 1 shows each of the sewering line 74, the water supply line 76, and the exhaust line 82 disposed within the ceiling 26 of the medical facility 20. Likewise, the offload pump 72 and the vacuum pump 80 are disposed within the ceiling 26 of the medical facility 20. With the offload pump 72 and the vacuum pump 80 integrated within the medical facility 20, space within the medical facility 20 preserved and sound associated the pumps is more effectively managed. Of course, other suitable locations of the components are contemplated and may be based, at least in part, on the existing architecture of the medical facility 20. For example, the offload pump and the vacuum pump may be located in an area outside of the medical facility 20.

In one variant, the second waste container may provide a large capacity reservoir for the liquid waste material emptied from the waste volume 58 of the first waste container 56. As a result, the second waste container may include a waste volume larger than the waste volume 58 of the first waste container 56. In such an arrangement, the second waste container is in fluid communication with the first waste container 56, the discharge line 90 and the offload pump 72. The second waste volume may also be in fluid communication with the sewering line 74 such that the second waste volume may service as an intermediate holding tank prior to sewering or permanent disposal of the liquid waste material. The offload pump 72 may be selectively operated to draw a vacuum through the discharge line 90 to transfer the liquid waste material from the first waste container 56 to the second waste container.

Returning to the waste container 56, the waste collection assembly 42 of the medical waste management system 40 includes a vacuum port 84 in fluid communication with the waste volume 58. The vacuum port 84, in the most general sense, may be an opening on or near the waste container 56 to be coupled to or arranged in fluid communication with a vacuum line 86 extending from the service head 54 to the vacuum pump 80 through the boom 46. The vacuum line 86 in fluid communication with the vacuum port 84 establishes fluid communication between the waste volume 58 and the vacuum pump 80. The waste collection assembly 42 further includes a discharge port 88 in fluid communication with the waste volume 58 of the waste container 56. The discharge port 88, in the most general sense, may be another opening on or near the waste container 56 to be coupled to or arranged in fluid communication with a discharge line 90 extending from the service head 54 to the offload pump 72 through the boom 46. The discharge line 90 in fluid communication with the discharge port 88 establishes fluid communication between the waste volume 58 and the offload pump 72. In the schematic representation of the medical waste management system 40 shown in FIG. 2, at least a portion of the vacuum line 86 and the discharge line 90 may be operably coupled with one or more valves 92a, 92b for controlling the vacuum provided from the offload pump 72 and the vacuum pump 80 to the discharge port 88 and the vacuum port 84, respectively, in a manner to be explained in greater detail. Alternatively, two separate lines may be provided with or without requiring the valves. Further, the waste collection assembly 42 of the medical waste management system 40 includes a cleaning port 94 in fluid communication with the waste volume 58 of the waste container 56. The cleaning port 94, in the most general sense, may be still another opening on or near the waste container 56 to be coupled to or arranged in fluid communication with the water supply line 76 extending to the service head 54 through the boom 46. Still further, the waste collection assembly 42 may be integrated with an electrical and/or electronic system of the medical facility 20 with power and/or data lines extending through the boom 46. The mount 44 may define a passageway for the aforementioned components extending through the boom 46 to pass through an opening within the fixed structure. With each of the fluid, electrical, and data lines extending through the boom 46 and the mount 44 to external to the medical facility 20, the medical waste management system 40 advantageously limits obstructions present in the medical facility 20 and provides for an aesthetically pleasing system. It should be appreciated that the fluid, electrical, and/or data lines need not be fully within the entire length of the boom 46. Instead, only a portion of the fluid, electrical, and/or data lines need to be within the boom 46 to take advantage of features of this disclosure.

Operation of the medical waste management system 40 will now be described with continued reference to FIGS. 1 and 2. With the patient positioned on the patient support surface 36 of the patient support apparatus 28, the service head 54 of the waste collection assembly 42 is moved into proximity with the patient. With the suction line 60 in fluid communication with the waste volume 58, the vacuum pump 80 is operated to provide a vacuum to the instrument 61 at the end of the suction line 60. The valves 92a, 92b may be actuated to provide fluid communication between the vacuum pump 80 and the waste volume 58. The vacuum includes a vacuum path through the vacuum line 86, the vacuum port 84, the waste volume 58, and the suction line 60, among other components to be described. The liquid waste material, for example blood or other bodily fluids, is drawn into the waste volume 58 under the influence of the vacuum. The liquid measuring system 62 may measure a level of the liquid waste material, and the user interface 52 may display the same.

Once the waste container is adequately filled with the waste material, and/or according to a disposal schedule or as desired, existing systems often require the waste collection assembly be transported to and docked with a remote disposal station to perform emptying and/or cleaning operations. The transport to and docking with the remote disposal station requires the attention and effort of hospital staff who could otherwise be performing other tasks with the medical facility, and further results in undesirable downtime of the waste collection assembly. The medical waste management system 40 of the present disclosure, in certain configurations, advantageously provides for operating the disposal system 68 to empty the waste container 56 of the liquid waste material collected within the waste volume 58 without need of transport of a cart outside the medical facility 20 and with little downtime. The offload pump 72 may be operated to provide another vacuum to the waste volume 58 through the discharge line 90 and the discharge port 88, among other components to be described. The valves 92a, 92b may be actuated to provide fluid communication between the offload pump 72 and the waste volume 58. The valves 92a, 92b providing fluid communication between the offload pump 72 and the waste volume 58 may prevent fluid communication between the vacuum pump 80 and the waste volume 58. Additionally or alternatively, operation of the vacuum pump 80 may be stopped prior to operating the offload pump 72.

The waste material collected within the waste volume 58 is moved through the discharge line 90 extending through the boom 46 to the sewering line 74 integrated with the medical facility 20. It is contemplated that the offload pump 72 and the vacuum pump 80 may be integrated into a single suction source. However, with the waste collection assembly 42 suspended from the ceiling 26, overcoming the gravitational forces in view of the cavitation associated with the liquid waste moving through the discharge line 90 may be particularly well suited for the aforementioned two pump arrangement.

During or after emptying the waste container 56 of the liquid waste material collected within the waste volume 58, it may be desirable to clean the waste container 56. The cleaning system 70 may be operated to provide water from the water supply line 76, detergent from the detergent reservoir 71, or a combination of the two. In one example, the water-detergent mixture is pumped with a cleaning system pump (not shown) to the waste volume 58 through the water supply line 76 extending through the boom 46 and through the cleaning supply port 94. The cleaning system 70 may further include at least one sprayer 96 coupled to the waste container 56 and in fluid communication with the cleaning supply port 94. FIG. 1 shows two sprayers 96 disposed within the waste volume 58. The sprayer(s) 96 discharge the water-detergent mixture within the waste volume 58, and in particular towards an inner surface of the water container 56 defining the waste volume 58. Specifics of the sprayer(s) 96 and related operation of the cleaning system 70 suitable for the present application is disclosed in commonly owned International Patent Publication No. WO 2017/112684, filed Dec. 20, 2016, hereby incorporated by reference in its entirety. The offload pump 72 may be concurrently or subsequently operated to empty the waste container 56 of the water-detergent mixture along with any residual liquid waste material.

The waste collection assembly 42 may include several additional components for optimizing operating and/or usability of the medical waste management system 40. The waste collection assembly 42 may include a suction inlet 98 in fluid communication with the waste volume 58 and the vacuum port 84, as shown in FIG. 2. The suction inlet 98 is configured to be arranged in fluid communication with a manifold 100 or other media. The manifold 100 shown in FIG. 1 may take the form of that disclosed in commonly owned U.S. Pat. No. 7,615,037, issued Nov. 10, 2009, hereby incorporated by reference in its entirety. The manifold 100, among other features, may filter semisolid and solid matter entrained within the liquid waste material received through the suction line 60 coupled to the manifold 100.

In certain implementations, the waste collection assembly 42 may include a manifold receiver 102 disposed on the service head 54 and define an opening in fluid communication with the suction inlet 98. The opening of the manifold receiver 102, in the most general sense, is configured to removably receive at least a portion of the manifold 100, for example as shown in FIG. 1, in a manner to provide fluid communication between an outlet of the manifold 100 and the suction inlet 98. One coupling arrangement between the manifold 100 and the manifold receiver 102 is disclosed in the aforementioned U.S. Pat. No. 7,615,037. The waste collection assembly 42 may include a data reader 103 (see, e.g., FIG. 5) on or near the manifold receiver 102. The data reader and complementary electronic componentry are configured to detect readable indicia on the manifold 100 or other media removably coupled to the service head 54, and transmit a signal to the controller to permit operation or control of the waste collection assembly 42 based on the signal. In one example, the readable indicia is an radiofrequency identification (RFID) tag coupled to the manifold 100 in which the controller determines, based on the signal from the data reader, whether the manifold 100 has previously been used, is authorized to be used with the waste collection assembly 42, and the like. Certain aspects of controlling operation of the waste collection assembly 42 based on data associated with readable indicia is disclosed in commonly owned International Patent Publication No. WO 2007/103842, filed Mar. 8, 2006, hereby incorporated by reference in its entirety.

Given the convenience and accessibility of positioning the waste collection assembly 42 near the patient support apparatus 28, it may be particularly desirable to glean information from the service head 54 regarding the operating state of the waste collection assembly 42 without undue difficulty. In certain implementations, the waste collection assembly 42 may include a light assembly 104 locating on the service head 54, for example, near the manifold receiver 102. FIG. 1 shows the light assembly 104 as a light ring extending around the opening of the manifold receiver 102, including the manifold 100 at least partially disposed within the opening. The light assembly 104 may be in communication with the controller with the controller configured to operate the light assembly 104 to emit light based on the operating state of the waste collection assembly 42. For example, the color or pattern of light may be different depending on the operating state. The light assembly 104 may also illuminate the manifold 100 or media itself when coupled to the service head 54. One suitable light assembly and methods of operating the same suitable for present application is disclosed in commonly owned United States Patent Publication No. 2016/0367732, filed Aug. 31, 2016, hereby incorporated by reference in its entirety.

The medical waste management system 40 may further include a vacuum regulator 106 located on the service head 54 or other location in/on the boom 46 and configured to regulate a level of the vacuum drawn on the waste volume 58 by the vacuum pump 80. Among other advantages, including the vacuum regulator 106 on the service head 54, as opposed to being integrated within the medical facility 20, may facilitate ease with service of the waste collection assembly 42 and retrofitting existing medical facilities 20 with the medical waste management system 40. One vacuum regulator suitable for the present application is disclosed in the aforementioned commonly owned U.S. Pat. No. 7,621,898, again hereby incorporated by reference in its entirety. The medical waste management system 40 may also include a filter 108, for example a HEPA filter, in communication with the vacuum line 86 and located between the waste 56 container and the vacuum pump 80, a muffler 110 or other sound attenuation features, additional valving 112, and the like (see, e.g., FIG. 4). Of particular interest are safety features to eliminate backflow of the liquid medical waste within the boom 46 and the waste collection assembly 42, and into possible contact with user or the patient. Exemplary safety features may include a vacuum breaker, a level sensor ensuring an air gap, check valves, and the like. Additional safety features may include relays and other electric componentry to operably decouple the pump(s) 72, 80 from ground to limit exposure of the patient to electrical shock, as the fluid path may act as a conductive path. The safety features may be incorporated in a manner to achieve Cardiac Floating (CF) classification pursuant to IEC60601-1 (Third Edition).

Figure 3:
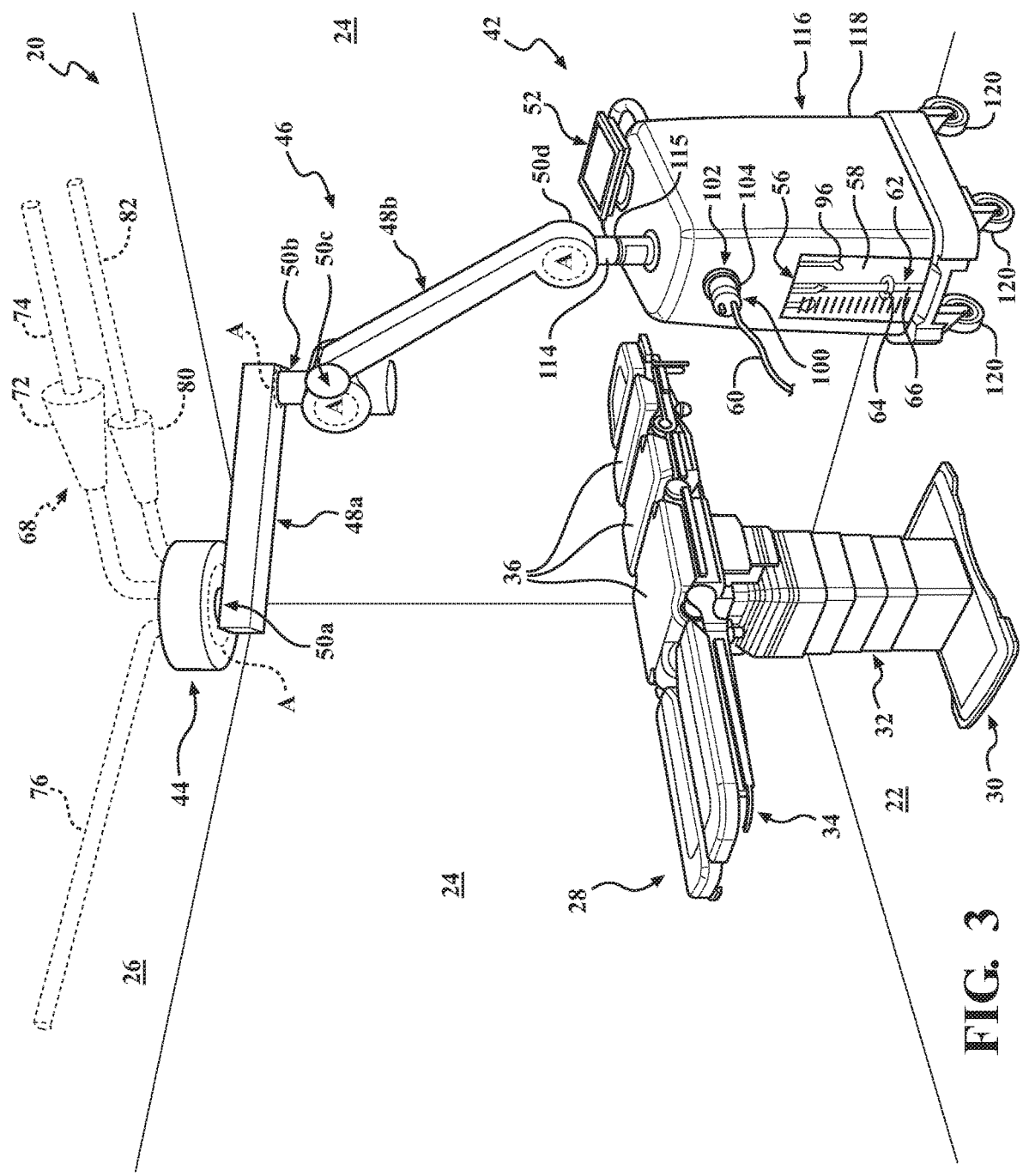
FIG. 3 is a perspective view of the medical facility and a medical waste management system.
Figure 4:
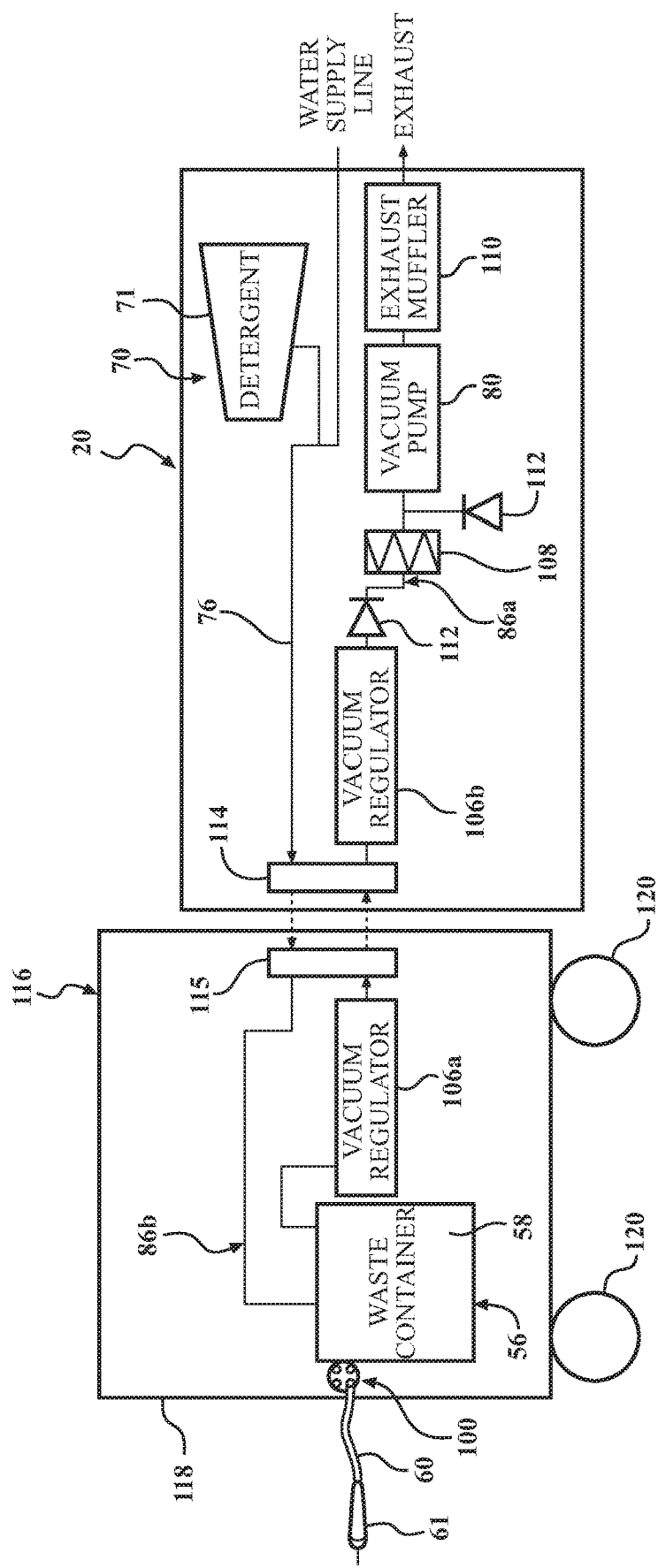
FIG. 4 a schematic representation of the medical waste management system of FIG. 3.
Figure 5:
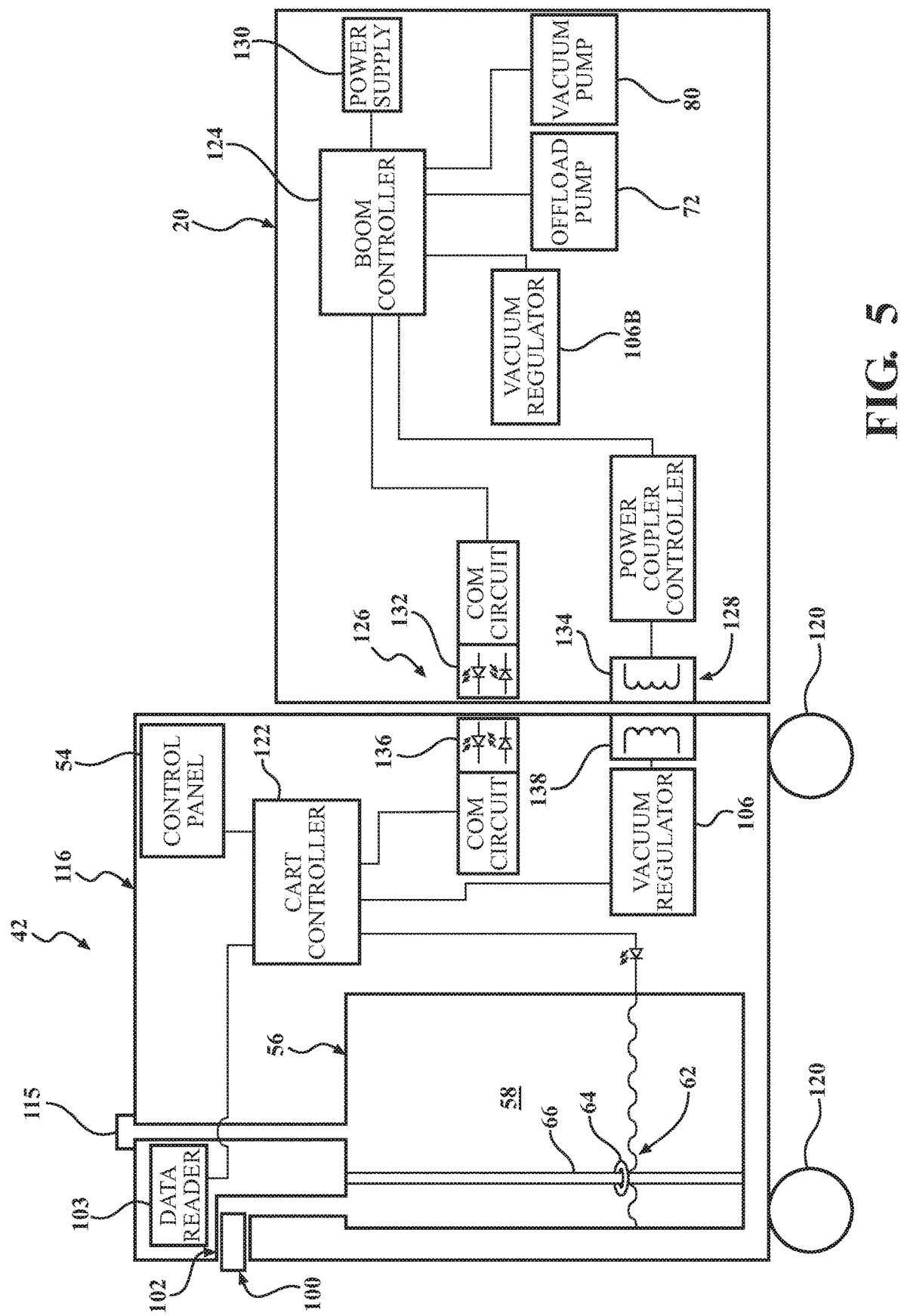
FIG. 5 is another schematic representation of the medical waste management system of FIG. 3.

Referring now to FIGS. 3-5, the medical waste management system 40 is similar to the previously described implementation with like numerals indicating like components. The medical waste management system 40 includes the mount 44 rigidly secured to the ceiling 26 of the medical facility 20. The boom 46 is secured to the mount 44 to be supported by and suspended from the ceiling 26. The boom 46 includes the elongate arms 48a, 48b coupled with the mount 44 and to one another at the joints 50a-50d to provide for positioning a coupling mechanism 114 disposed at a second end of the second elongate arm 48b at a desired position within the medical facility 20. The sewering line 74, the water supply line 76, and the exhaust line 82 may be integrated with the medical facility 20 in the manner previously described with the vacuum line 86, the discharge line 90, and the water supply line 76 at least partially extending through the mount 44 and the boom 46 to the coupling mechanism 114.

The waste collection assembly 42 may be supported on a mobile cart 116, as shown in FIG. 3. The mobile cart 116 includes a base 118, and wheels 120 coupled to the base 118 for moving the mobile cart 116 along the floor surface 22 of the medical facility 20. The waste container 56 defining the waste volume 58 is supported on the mobile cart 116. The liquid measuring system 62 and the sprayer(s) 96 of the cleaning system 70 may be coupled to the waste container 56 and disposed within the waste volume 58. The mobile cart 116 may include the manifold receiver 102 defining the opening configured to receive at least a portion of the manifold 100. FIG. 3 shows the manifold 100 extending from a front of the mobile cart 116 with the suction line 60 coupled to the manifold 100. The light assembly 104 is positioned on the mobile cart 116 near the manifold receiver 102 to emit light based on the operating state of the waste collection assembly 42, and perhaps illuminate the manifold 100 or other media when coupled to the mobile cart 116. The user interface 52 may be supported on the mobile cart 116.

The mobile cart 116 includes a coupling mechanism 115 complementary to the coupling mechanism 114 of the boom 46. The complementary coupling mechanisms 114, 115 are configured to removably couple to one another to establish fluid communication between the waste volume 58 and the vacuum pump 80. With reference to FIG. 4 schematically illustrating fluid flow paths of each of the mobile cart 116 and the medical facility 20, the coupling mechanism 115 of the mobile cart 116 is in fluid communication with the waste volume 58. Likewise, the coupling mechanism 114 on the boom 46 is in fluid communication with the vacuum pump 80 via the vacuum line 86. The complementary coupling mechanisms 114, 115 include features, for example openings with valves configured to provide fluid communication across the interface, and thus between the waste volume 58 and the vacuum pump 80. One suitable complementary coupling mechanism arrangement for establishing fluid communication between the mobile cart 116 and the boom 46 is disclosed in commonly owned U.S. Pat. No. 10,105,470, issued Oct. 23, 2018, hereby incorporated by reference in entirety.

In certain implementation, the vacuum regulator 106a may be supported on the mobile cart 116. As previously mentioned, the vacuum regulator 106a is configured to regulate the level of the vacuum drawn on the waste volume 58 by the vacuum pump 80. In such an implementation, the vacuum regulator 106a may be arranged in fluid communication when the mobile cart 116 and the boom 46 are docked, i.e., the complementary coupling mechanisms 114, 115 are coupled. Additionally or alternatively, the vacuum regulator (or another vacuum regulator 106b) may be integrated with the medical facility 20 in manners previously described, as schematically represented in FIGS. 4 and 5.

With the waste collection assembly 42 disposed on the mobile cart 116, it is readily appreciated certain electronic components are correspondingly disposed on the mobile cart 116. For example, the liquid measuring system 62 including the float element 64 and sensor rod 66 detects the level of the liquid waste material within the waste volume 58 and provides a signal corresponding to the controller. As such, it may be desirable to have the controller 122 supported on the mobile cart 116 (i.e., a cart controller). Moreover, the electronic components including the cart controller 122 require electric power to operate. It is further readily appreciated that certain electronic components integrated with the medical facility 20 also require electric power to operate, for example the vacuum pump 80 and the offload pump 72, and the vacuum regulator 106b when applicable. As such, it may be desirable to have a controller 124 integrated with the medical facility 20 (i.e., a boom controller) to direct electric power to the components. The boom controller 124 may be configured control electronic components based on the operating state of the waste collection assembly 42 as determined by the cart controller 122. Consequently, the medical waste management system 40 may be provide for establishing an electronic communications circuit 126 and/or a power delivery circuit 128 when the complementary coupling mechanisms 114, 115 are removably engaged. In one example, the boom controller 124 may control one or more of the vacuum pump 80 and the vacuum regulator 106b based on the level of the liquid waste material within the waste volume 58 as measured by the liquid measuring system 62.

With continued reference to FIG. 5, the boom controller 124 is in communication with a power supply 130, which may be integrated with the main power system of the medical facility 20. The boom controller 124 is further in communication with a data coupler 132 of the electronic communications circuit 126, and a power coupler 134 of the power delivery circuit 128. The cart controller 122 is further in communication with a complementary data coupler 136 of the electronic communications circuit 126, and a power coupler 138 of the power delivery circuit 128. With the boom 46 removably coupled to the mobile cart 116 with the complementary coupling mechanisms 114, 115, the electronic communications circuit 126 is established between the cart controller 122 and the boom controller 124, and the power delivery circuit 128 is established between the power supply 130 and the electronic componentry on the mobile cart 116. One power and data coupling interface suitable for the present application is disclosed in the aforementioned U.S. Pat. No. 10,105,470, again hereby incorporated by reference. Further, the electronic communications circuit 126 may further include establishing communication between the user interface 52 supported on the mobile cart 116 with the boom controller 124 integrated within the medical facility 20. In such an arrangement, with the mobile cart 116 coupled to the boom 46, the user may provide an input to the user interface 52 to control components integrated within the medical facility 20, thereby providing ease of use of the medical waste management system 40.

An exemplary operation of the medical waste management system 40 may include transporting the mobile cart 116 into the medical facility 20. The mobile cart 116 is positioned as desired near the patient support apparatus 28, for example, as shown in FIG. 3. The manifold 100 is removably engaged with the manifold receiver 102. Based on the presence of the manifold 100 as detected by the data reader 103 in communication with the cart controller 122, the cart controller 122 may enable to the waste collection assembly 42 to be operated. Otherwise, for example, if the manifold 100 is not authentic or previously used, the cart controller 122 may disable operation of the waste collection assembly 42. The cart controller 122 may operate the light assembly 104 to emit light to alert the user the manifold 100 is properly engaged with the manifold receiver 102 and/or the waste collection assembly 42 is operable.

The boom 46 is moved to a desired position to be operably coupled with the mobile cart 116, either manually or by operation of the actuators A in communication with the boom controller 124. The complementary coupling mechanisms 114, 115 are engaged to establish the electronic communications circuit 126 and the power delivery circuit 128. The boom controller 124 operates the vacuum pump 80 to provide a vacuum to the instrument 61 at the end of the suction line 60. The vacuum includes a vacuum path through the first vacuum line 86a, a second vacuum line 86b within the mobile cart 116, the vacuum port 84, the waste volume 58, and the suction line 60. The liquid waste material, for example blood or other bodily fluids, is drawn into the waste volume 58 under the influence of the vacuum. The liquid measuring system 62 may measure a level of the liquid waste material, and the user interface 52 may display the same. The liquid measuring system 62 may provide a corresponding signal to the cart controller 122.

In certain implementations, emptying and/or cleaning of the waste volume 58 may include transporting the mobile cart 116 to a remote disposal station (not shown). In such an arrangement, it may not be necessary for the medical waste management system 40 to include the disposal system 68 and/or the cleaning system 70 integrated within the medical facility 20, thereby simplifying the architecture required to install or retrofit the medical waste management system 40 within the medical facility 20. In certain implementations, the disposal system 68 and/or the cleaning system 70 is provided as previously described. Once the waste container is adequately filled with the waste material, and/or according to a disposal schedule or as desired, the cart controller 122 may transmit a signal to the boom controller 124 to operate the offload pump 72 to provide another vacuum to the waste volume 58. The waste material collected within the waste volume 58 is moved through the discharge port 88, the complementary coupling mechanisms 114, 115 and through the boom 46 to the sewering line 74 integrated with the medical facility 20. Furthermore, the cart controller 122 may transmit another signal to the boom controller 124 to operate the cleaning system 70 to provide water from the water supply line 76, detergent from the detergent reservoir 71, or a combination of the two, through the boom 46, the cleaning supply port 94, the sprayer(s) 96, and into the waste volume 58.

It is further contemplated that, in one variant, the boom 46 and the mobile cart 116 may be semi-permanently or fixedly coupled to one another. In other words, it is not intended for the mobile cart 116 to often be decoupled from the boom 46. In such an arrangement, the boom 46 moves with movement of the mobile cart 116 along the floor surface 22 to function more akin to a line management system, thereby limiting obstructions within the medical facility 20.

Figure 6:
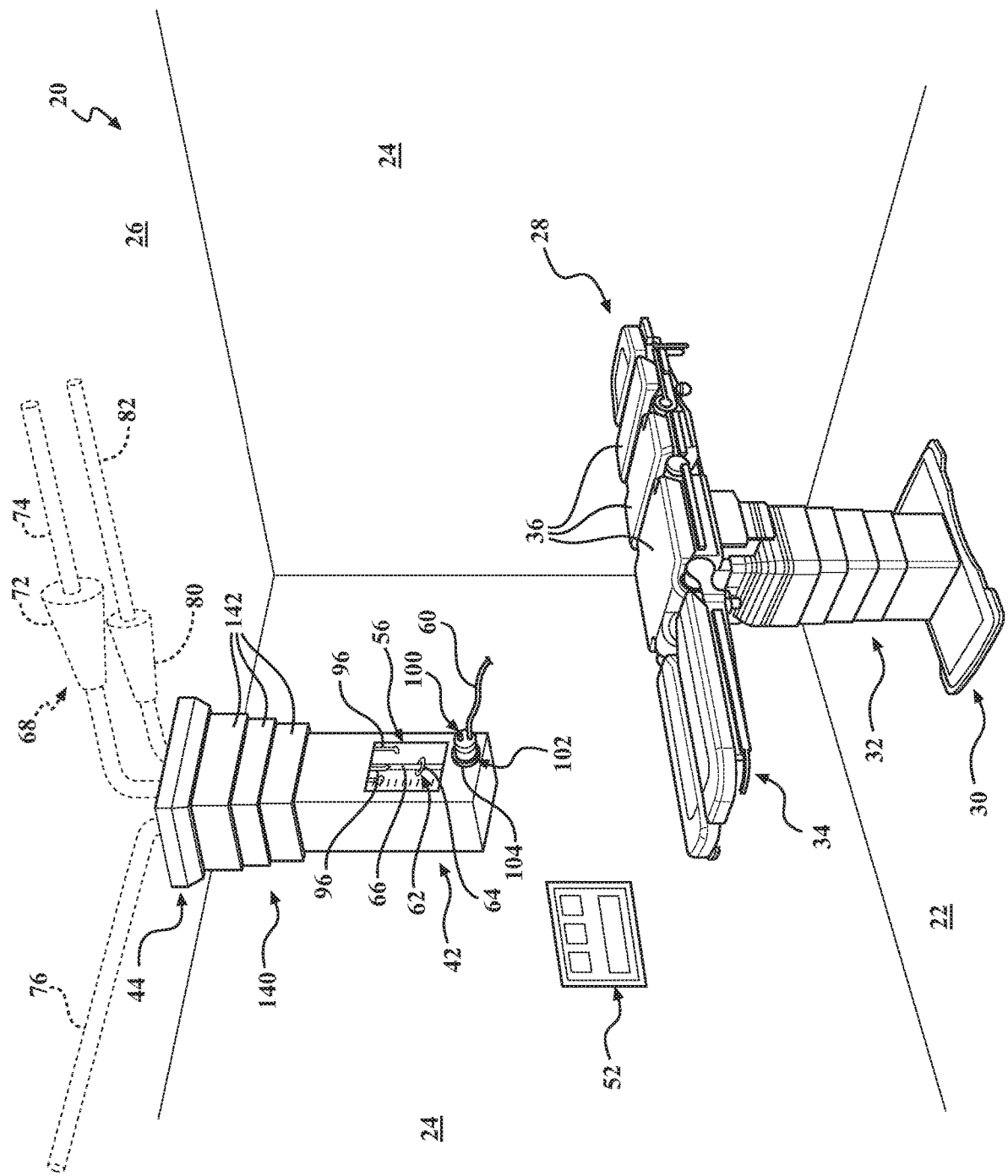
FIG. 6 is a perspective view of the medical facility and a medical waste management system.

FIGS. 6-9 illustrate the medical waste management system 40 being in at least some respects similar to the previously described implementations with like numerals indicating like components and with the corresponding description of the like components hereby incorporated by reference. FIG. 6 shows the waste collection assembly 42 assuming a form factor similar to that of medical column 140 supported from the ceiling 26 of the medical facility 20. The medical column 140 may include one or more telescoping sections 142 movable relative to one another to permit adjustment of a height at which the waste collection assembly 42 is suspended from the ceiling 26. The illustrated mount 44 of the medical column 140 is rigidly fixed to the ceiling 26, but it is contemplated that a rail system (not shown) may be provided to permit lateral movement of the medical column 140 within the medical facility 20. The user interface 52 (and/or a second user interface) may be provided on the wall 24 of the medical facility 20.

Figure 7:
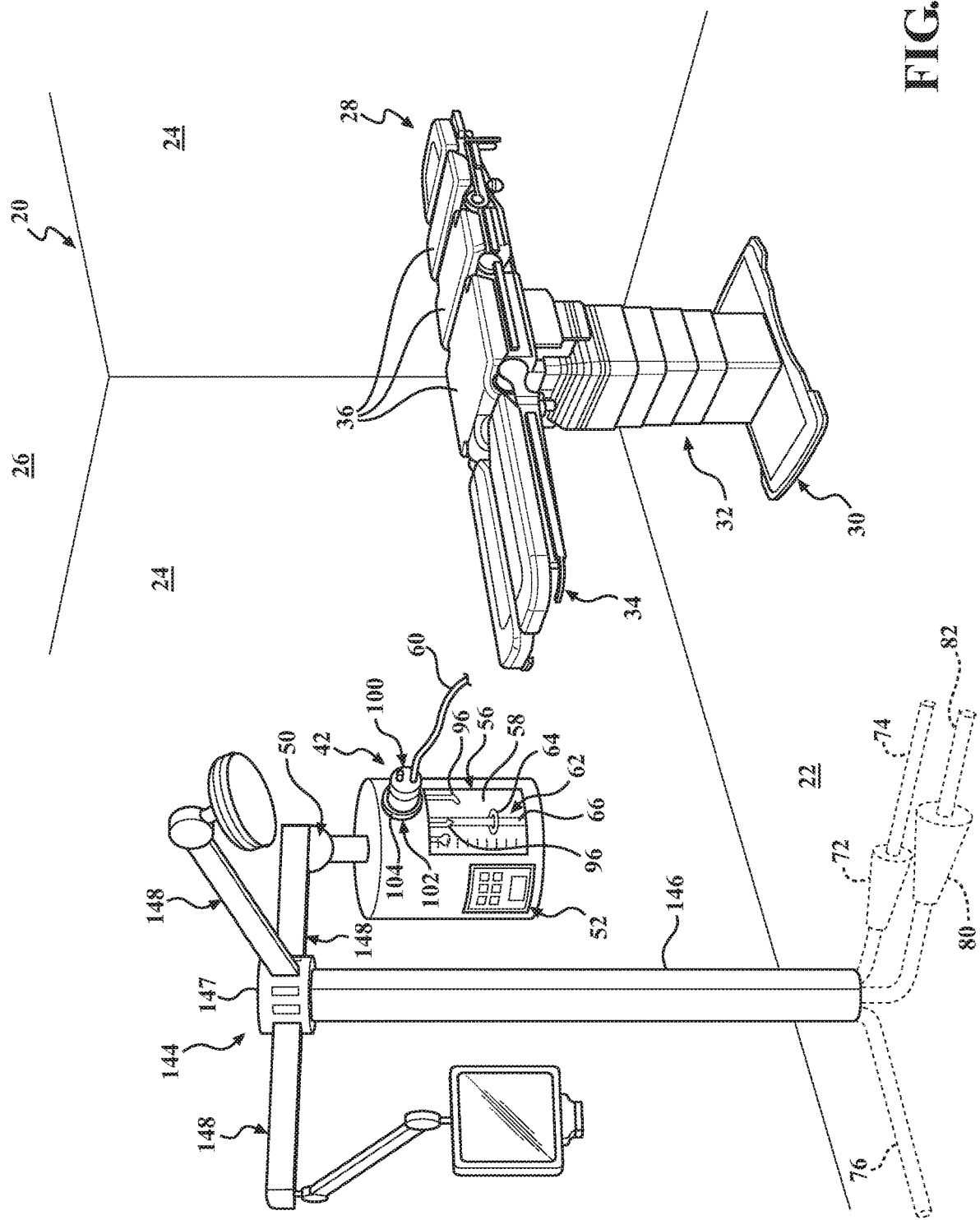
FIG. 7 is a perspective view of the medical facility and a medical waste management system.

FIG. 7 shows the waste collection assembly 42 coupled to a support frame 144 supported on the floor surface 22 of the medical facility 20. The support frame 144 may assume any suitable construction, for example, an elongated column 146 rigidly coupled to and extending upwardly from the floor surface 22. The elongated column 146 may be tubular in form so as to permit the passage of various components of the medical waste management system 40 (e.g., the water supply line 76). A head 147 is supported at a top of the elongated column 146, and one or more elongated arms 148 extend from the head 147. One of the elongated arms 148 may support the waste collection assembly 42, and other elongated arms 148 may support other components of the medical waste management system 40 or other medical accessories (e.g., a monitor, a lamp, etc.).

Figure 8:
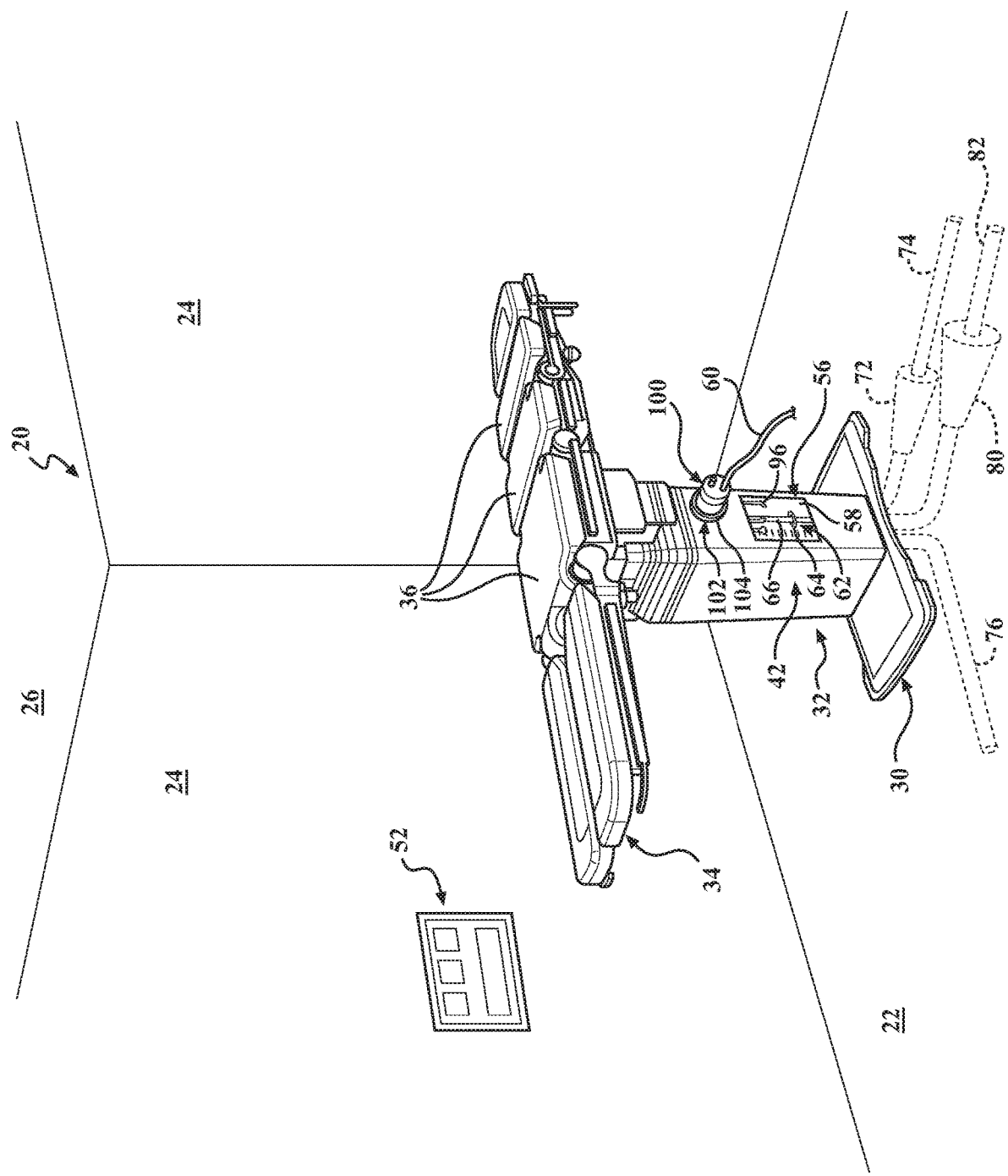
FIG. 8 is a perspective view of the medical facility and a medical waste management system.

FIG. 8 shows the waste collection assembly 42 integrated with the patient support apparatus 28 rigidly supported on the floor surface 22 of the medical facility 20. In particular, the waste container 56 is at least partially disposed within the intermediate frame 32 of the patient support apparatus 28. Further, the manifold receiver 102 is also disposed within the intermediate frame 32 of the patient support apparatus 28 and in fluid communication with the waste volume 58 defined by the waste container 56. As a result, the suction tube 60 operably coupled to the manifold 100 removably engaged with the manifold receiver 102 is near the patient support surface 36 without requiring additional footprint on the floor surface 22 and without obstruction from overhead. The disposal system 68 including the offload pump 72 and the cleaning system 70 including the water supply line 76 may extend through the base 30 of the patient support apparatus 28 to be integrated beneath the floor surface 22 of the medical facility 20. The user interface 52 being disposed on the wall 24 of the medical facility 20 may be desired based on the location of the waste collection assembly 42 relative to the floor surface 22.

Figure 9:
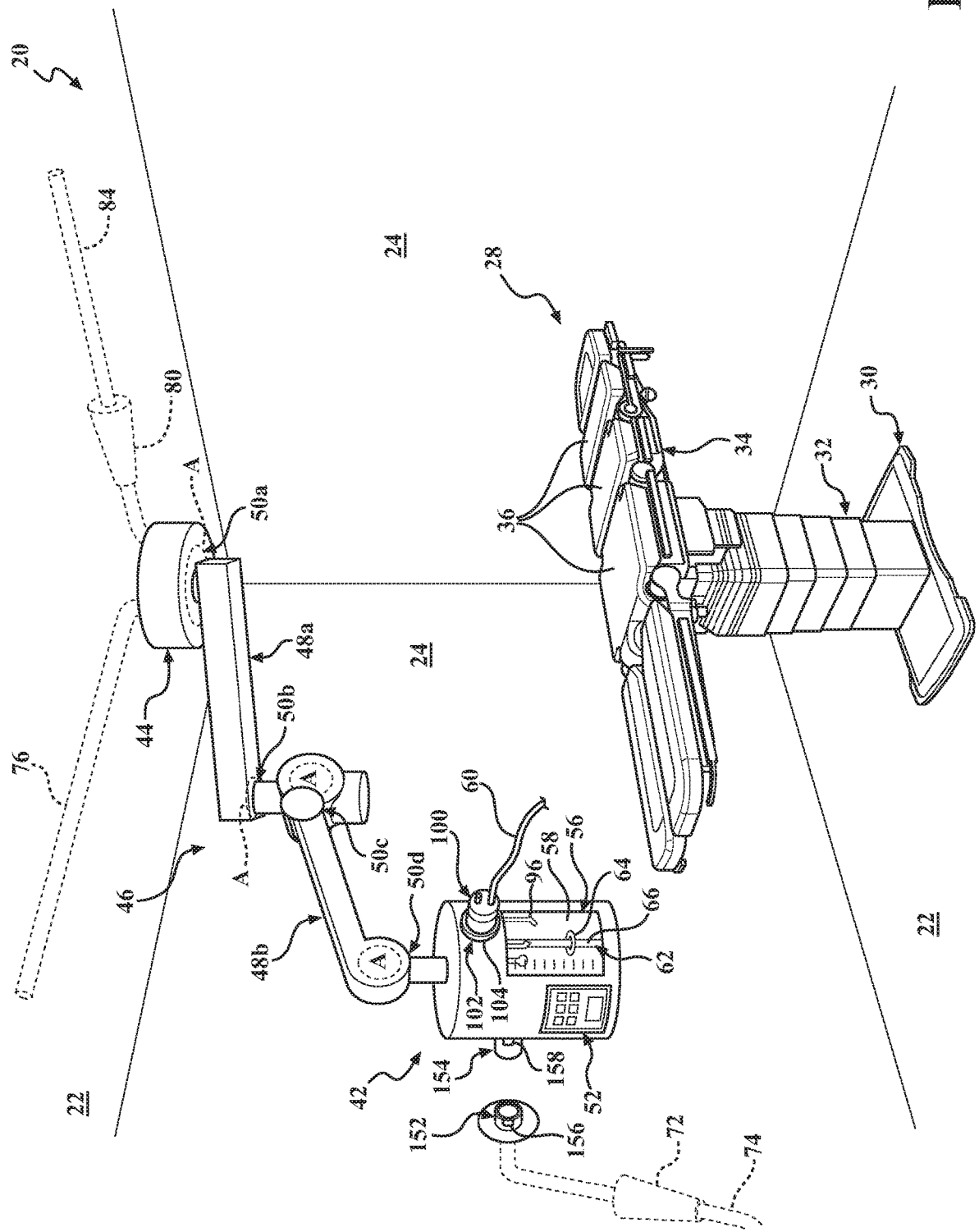
FIG. 9 is a perspective view of the medical facility and a medical waste management system.

FIG. 9 shows the medical waste management system 40 including the disposal system 68 with an inlet port 152 on the fixed structure of the medical facility 20. In particular, the boom 46 is mounted to the ceiling 26 of the medical facility 20 with the mount 44, and the inlet port 152 is coupled to the wall 24 of the medical facility 20. The inlet port 152 is in fluid communication with the discharge line 90 and the offload pump 72 as shown. The waste collection assembly 42 includes an outlet port 154 in fluid communication with the waste volume 58. Further, complementary coupling mechanisms 156, 158 are associated with each of the inlet port 152 and the outlet port 154 and configured to be removably engaged to one another. FIG. 9 shows the coupling mechanism 158 of the waste collection assembly 42 disposed on the service head 54, and the coupling mechanism 158 positioned adjacent the inlet port 152 on the wall 24. When removably engaged, the complementary coupling mechanisms 156, 158 provide a fluid-tight seal and establish a fluid communication path between the inlet and outlet ports 152, 154, and thereby the waste volume 58 and the discharge line 90. In such an implementation, the vacuum pump 80 is operated in manners previously described to draw a vacuum through the vacuum line 86 such that the liquid waste material is drawn through the suction line 60 and into the waste volume 58. Typically subsequent to completion of the surgical procedure, the operation of the vacuum pump 80 is stopped. The boom 46 is moved to position the waste container 56, with the waste material within the waste volume 58, in proximity with the inlet port 152. The complementary coupling mechanisms 156, 158 are removably engaged to establish the fluid communication between the waste volume 58, the outlet port 154, the inlet port 152, and the discharge line 90. The offload pump 72 is operated to draw another vacuum such that the liquid waste material is drawn from the waste container 56 and through the discharge line 90, for example, to the sewering line 74. Among other advantages, the need for the liquid waste material to be moved against the force of gravity is limited or eliminated, thereby limiting the risk of inadvertent backflow through the boom 46. It is further contemplated that the cleaning system 70 may be operated across the inlet and outlet port 152, 154 interface as opposed to through the boom 46. The waste collection assembly 42 may remain docked with the complementary coupling mechanisms 156, 158 engaged until required for subsequent duty, thereby storing the waste collection assembly 42 at a consistent location that limits obstruction within the medical facility 20.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:
1. A medical waste management system comprising:
a mount configured to be rigidly secured to a fixed structure of a medical facility;
a boom secured to said mount and comprising at least one elongated arm for extending away from the fixed structure;
a service head coupled to said boom;

a waste container located on said service head and defining a waste volume sized to collect liquid waste material during a medical procedure performed within the medical facility with the liquid waste material being received through a suction line under influence of a vacuum provided by a vacuum pump;

a vacuum port in fluid communication with said waste volume;

a vacuum line disposed within said boom and configured to establish fluid communication between said vacuum port and the vacuum pump;

a liquid measuring system located on said service head and within said waste volume with said liquid measuring system configured to measure a level of the liquid waste material within said waste volume;

a discharge port in fluid communication with said waste volume and configured to be coupled to a discharge line to establish fluid communication between said waste volume and a disposal system;

a valve located on said service head and operably coupled to the vacuum port and the discharge port, the valve configured for controlling the vacuum provided to both the discharge port and the vacuum port.

2. The medical waste management system of claim 1, wherein said at least one elongate arm of said boom comprises at least two elongated arms coupled to one another at one or more joints providing relative articulation between said elongated arms with an end of one of said elongated arms secured to said mount and an end of another one of said elongated arms coupled to said service head.

3. The medical waste management system of claim 1, further comprising a cleaning supply port in fluid communication with said waste volume and configured to be coupled to a water supply line to establish fluid communication between said waste volume and a source of water.

4. The medical waste management system of claim 3, further comprising a cleaning system and comprising at least one sprayer coupled to said waste container and in fluid communication with said cleaning supply port.

5. The medical waste management system of claim 4, wherein said cleaning system further comprises a detergent reservoir configured to be in fluid communication with said cleaning supply port.

6. The medical waste management system of claim 1, further comprising a suction inlet in fluid communication with said waste volume and said vacuum port with said suction inlet configured to be removably coupled with a manifold.

7. The medical waste management system of claim 1, further comprising a vacuum regulator located on said service head and configured to regulate a level of the vacuum drawn on said waste volume by the vacuum pump.

8. The medical waste management system of claim 1, further comprising a user interface located on said service head with said user interface configured to receive input from a user and display information to the user.

9. The medical waste management system of claim 1, wherein the service head is configured to removably receive media, and wherein the medical waste management system further comprises a light assembly located on said service head and positioned to illuminate the media when removably coupled with said service head.

10. The medical waste management system of claim 1, wherein the service head is configured to removably receive media, and wherein the medical waste management system further comprises a data reader located on said service head and positioned to detect readable indicia disposed on the media when removably coupled with said service head.

11. The medical waste management system of claim 1, wherein the fixed structure of the medical facility is one of a ceiling, a wall, and a floor surface of a medical facility.

* * * * *